(12) United States Patent
Zeegers (10) Patent No.: US 8,974,532 B2
(45) Date of Patent: *Mar. 10, 2015

(54) INTERVERTEBRAL DISC PROSTHESIS

(75) Inventor: M. Willem Zeegers, Meerssen (NL)

(73) Assignee: LDR Medical, Rosiéres Prés Troyes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/215,123

(22) Filed: Aug. 22, 2011

(65) Prior Publication Data

US 2012/0053693 A1    Mar. 1, 2012

Related U.S. Application Data

(63) Continuation of application No. 12/391,086, filed on Feb. 23, 2009, now Pat. No. 8,002,835, and a continuation-in-part of application No. 11/098,266, filed on Apr. 4, 2005, now Pat. No. 7,494,508.

(30) Foreign Application Priority Data

Apr. 28, 2004   (FR) ...................... 04 04501

(51) Int. Cl.
*A61F 2/44*    (2006.01)
*A61F 2/30*    (2006.01)

(52) U.S. Cl.
CPC ..... *A61F 2/4425* (2013.01); *A61F 2002/30362* (2013.01); *A61F 2002/3039* (2013.01);
(Continued)

(58) Field of Classification Search
CPC ....... A61F 2/44; A61F 2/4405; A61F 2/4425; A61F 2002/44; A61F 2002/442; A61F 2002/4425

USPC ................. 623/17.11–17.16; 606/246–249
See application file for complete search history.

(56) References Cited

U.S. PATENT DOCUMENTS 3,374,786 A   3/1968  Callender et al.
3,791,380 A   2/1974  Dawidowski
(Continued)

FOREIGN PATENT DOCUMENTS

CA    2472708    2/2005
CA    2533473    3/2011
(Continued)

OTHER PUBLICATIONS

World Intellectual Property Organization; Written Opinion of the International Searching Authority for PCT Pub'n No. WO2005104996, App'n. No. PCT/IB2005/01151; Sep. 12, 2005; WIPO; Geneva, Switzerland; all pages.
(Continued)

*Primary Examiner* — Alvin Stewart
(74) *Attorney, Agent, or Firm* — Denko Coburn Lauff LLP (57) ABSTRACT

The present invention relates to an intervertebral disc prosthesis preferably comprising at least three pieces including an upper plate (1), a lower plate (2) and a mobile core (3) at least in relation to the lower plate (2), co-operation means (23, 33) allowing to limit or eliminate the movements of the core (3) in relation to the lower plate (2), in translation and in rotation, respectively, about an axis substantially parallel to the lower plate (2) and about an axis substantially perpendicular to the lower plate (2), at least one part of the surface of at least one plate being concave and complementary with a convex surface (30) of the core (3), with which it is in contact, wherein the tip (31) of the convex surface (30) of the core (3) is off center, in at least one direction, in relation to the center (32) of this convex surface (30).

20 Claims, 3 Drawing Sheets (52) U.S. Cl.
CPC ............... *A61F2002/30563* (2013.01); *A61F 2002/30616* (2013.01); *A61F 2002/3065* (2013.01); *A61F 2002/30654* (2013.01); *A61F 2002/443* (2013.01); *A61F 2220/0025* (2013.01); *A61F 2220/0033* (2013.01)
USPC ..................................................... 623/17.15

(56) References Cited

U.S. PATENT DOCUMENTS

| | | | |
|---|---|---|---|
| 3,892,232 A | 7/1975 | Neufeld | |
| 4,009,712 A | 3/1977 | Burstein et al. | |
| 4,135,506 A | 1/1979 | Ulrich | |
| 4,175,555 A | 11/1979 | Herbert | |
| 4,237,875 A | 12/1980 | Termanini | |
| 4,379,451 A | 4/1983 | Getscher | |
| 4,409,974 A | 10/1983 | Freedland | |
| 4,432,358 A | 2/1984 | Fixel | |
| 4,488,543 A | 12/1984 | Tornier | |
| 4,494,535 A | 1/1985 | Haig | |
| 4,519,100 A | 5/1985 | Wills et al. | |
| 4,561,432 A | 12/1985 | Mazor | |
| 4,612,920 A | 9/1986 | Lower | |
| 4,621,629 A | 11/1986 | Koeneman | |
| 4,632,101 A | 12/1986 | Freedland | |
| 4,653,489 A | 3/1987 | Tronzo | |
| 4,657,001 A | 4/1987 | Fixel | |
| 4,721,103 A | 1/1988 | Freedland | |
| 4,759,352 A | 7/1988 | Lozier | |
| 4,787,378 A | 11/1988 | Sodhi | |
| 4,791,918 A | 12/1988 | Von Hasselbach | |
| 4,898,156 A | 2/1990 | Gatturna et al. | |
| 4,946,468 A | 8/1990 | Li | |
| 4,964,403 A | 10/1990 | Karas et al. | |
| 4,968,315 A | 11/1990 | Gatturna | |
| 4,969,887 A | 11/1990 | Sodhi | |
| 4,973,332 A | 11/1990 | Kummer | |
| 4,973,333 A | 11/1990 | Treharne | |
| 5,002,550 A | 3/1991 | Li | |
| 5,007,910 A | 4/1991 | Anapliotis et al. | |
| 5,032,125 A | 7/1991 | Durham et al. | |
| 5,041,114 A | 8/1991 | Chapman et al. | |
| 5,041,116 A | 8/1991 | Wilson | |
| 5,046,513 A | 9/1991 | Gatturna et al. | |
| 5,057,103 A | 10/1991 | Davis | |
| 5,062,851 A | 11/1991 | Branemark | |
| 5,087,266 A | 2/1992 | Connell et al. | |
| 5,098,433 A | 3/1992 | Freedland | |
| 5,116,336 A | 5/1992 | Frigg | |
| 5,129,901 A | 7/1992 | Decoste | |
| 5,176,681 A | 1/1993 | Lawes et al. | |
| 5,192,303 A | 3/1993 | Gatturna et al. | |
| 5,207,679 A | 5/1993 | Li | |
| 5,217,486 A | 6/1993 | Rice et al. | |
| 5,242,448 A | 9/1993 | Pettine et al. | |
| 5,300,074 A | 4/1994 | Frigg | |
| 5,314,477 A * | 5/1994 | Marnay | 623/17.15 |
| 5,324,292 A | 6/1994 | Meyers | |
| 5,342,394 A | 8/1994 | Matsuno et al. | |
| 5,356,410 A | 10/1994 | Pennig | |
| 5,356,413 A | 10/1994 | Martins et al. | |
| 5,372,599 A | 12/1994 | Martins | |
| 5,417,692 A | 5/1995 | Goble et al. | |
| 5,417,712 A | 5/1995 | Whittaker et al. | |
| 5,429,641 A | 7/1995 | Gotfried | |
| 5,437,674 A | 8/1995 | Worcel et al. | |
| 5,443,514 A | 8/1995 | Steffee | |
| 5,456,721 A | 10/1995 | Legrand | |
| 5,458,601 A | 10/1995 | Young, Jr. et al. | |
| 5,472,452 A | 12/1995 | Trott | |
| 5,478,342 A | 12/1995 | Kohrs | |
| 5,489,210 A | 2/1996 | Hanosh | |
| 5,507,754 A | 4/1996 | Green et al. | |
| 5,507,816 A * | 4/1996 | Bullivant | 623/17.15 |
| 5,522,845 A | 6/1996 | Wenstrom, Jr. | |
| 5,531,792 A | 7/1996 | Huene | |
| 5,534,004 A | 7/1996 | Santangelo | |
| 5,549,617 A | 8/1996 | Green et al. | |
| 5,554,191 A | 9/1996 | Lahille et al. | |
| 5,562,689 A | 10/1996 | Green et al. | |
| 5,562,738 A * | 10/1996 | Boyd et al. | 623/17.15 |
| 5,571,104 A | 11/1996 | Li | |
| 5,571,189 A | 11/1996 | Kuslich | |
| 5,578,035 A | 11/1996 | Lin | |
| 5,591,168 A | 1/1997 | Judet et al. | |
| 5,593,409 A | 1/1997 | Michelson | |
| 5,613,974 A | 3/1997 | Andreas et al. | |
| 5,620,012 A | 4/1997 | Benderev et al. | |
| 5,643,321 A | 7/1997 | McDevitt | |
| 5,683,464 A | 11/1997 | Wagner et al. | |
| 5,702,449 A | 12/1997 | McKay | |
| 5,766,253 A | 6/1998 | Brosnahan, III | |
| 5,800,550 A | 9/1998 | Sertich | |
| 5,895,427 A | 4/1999 | Kuslich et al. | |
| 5,968,098 A | 10/1999 | Winslow | |
| 5,980,522 A | 11/1999 | Koros et al. | |
| 6,099,531 A | 8/2000 | Bonutti | |
| 6,102,950 A | 8/2000 | Vaccaro | |
| 6,129,763 A | 10/2000 | Chauvin et al. | |
| 6,146,421 A * | 11/2000 | Gordon et al. | 623/17.15 |
| 6,214,050 B1 | 4/2001 | Huene | |
| 6,241,769 B1 | 6/2001 | Nicholson et al. | |
| 6,302,914 B1 | 10/2001 | Michelson | |
| 6,368,350 B1 * | 4/2002 | Erickson et al. | 623/17.14 |
| 6,419,703 B1 | 7/2002 | Fallin et al. | |
| 6,419,706 B1 | 7/2002 | Graf | |
| 6,423,063 B1 | 7/2002 | Bonutti | |
| 6,447,544 B1 | 9/2002 | Michelson | |
| 6,447,546 B1 | 9/2002 | Bramlet et al. | |
| 6,485,517 B1 | 11/2002 | Michelson | |
| 6,500,205 B1 | 12/2002 | Michelson | |
| 6,517,580 B1 * | 2/2003 | Ramadan et al. | 623/17.15 |
| 6,527,804 B1 * | 3/2003 | Gauchet et al. | 623/17.12 |
| 6,540,753 B2 | 4/2003 | Cohen | |
| 6,558,423 B1 | 5/2003 | Michelson | |
| 6,558,424 B2 | 5/2003 | Thalgott | |
| 6,565,605 B2 | 5/2003 | Goble et al. | |
| 6,582,468 B1 * | 6/2003 | Gauchet | 623/17.16 |
| 6,599,294 B2 | 7/2003 | Fuss et al. | |
| 6,607,530 B1 | 8/2003 | Carl et al. | |
| 6,648,893 B2 | 11/2003 | Dudasik | |
| 6,679,887 B2 | 1/2004 | Nicholson et al. | |
| 6,706,068 B2 * | 3/2004 | Ferree | 623/17.11 |
| 6,709,458 B2 | 3/2004 | Michelson | |
| 6,716,247 B2 | 4/2004 | Michelson | |
| 6,723,128 B2 | 4/2004 | Uk | |
| 6,749,635 B1 * | 6/2004 | Bryan | 623/17.16 |
| 6,749,636 B2 | 6/2004 | Michelson | |
| 6,770,096 B2 | 8/2004 | Bolger et al. | |
| 6,793,679 B2 | 9/2004 | Michelson | |
| 6,805,714 B2 | 10/2004 | Sutcliffe | |
| 6,808,537 B2 | 10/2004 | Michelson | |
| 6,835,206 B2 | 12/2004 | Jackson | |
| 6,849,093 B2 | 2/2005 | Michelson | |
| 6,890,355 B2 | 5/2005 | Michelson | |
| 6,899,735 B2 * | 5/2005 | Coates et al. | 623/17.16 |
| 6,902,580 B2 | 6/2005 | Fallin et al. | |
| 6,916,340 B2 | 7/2005 | Metzger et al. | |
| 6,923,811 B1 | 8/2005 | Carl et al. | |
| 6,923,830 B2 | 8/2005 | Michelson | |
| 6,936,071 B1 * | 8/2005 | Marnay et al. | 623/17.15 |
| 6,955,691 B2 | 10/2005 | Chae et al. | |
| 6,962,606 B2 | 11/2005 | Michelson | |
| 6,966,929 B2 * | 11/2005 | Mitchell | 623/17.11 |
| 6,972,019 B2 | 12/2005 | Michelson | |
| 6,972,035 B2 | 12/2005 | Michelson | |
| 6,981,975 B2 | 1/2006 | Michelson | |
| 6,986,789 B2 * | 1/2006 | Schultz et al. | 623/17.15 |
| 7,001,385 B2 | 2/2006 | Bonutti | |
| 7,001,432 B2 * | 2/2006 | Keller et al. | 623/17.14 |
| 7,008,453 B1 | 3/2006 | Michelson | |
| 7,033,394 B2 | 4/2006 | Michelson | |
| 7,041,135 B2 | 5/2006 | Michelson | |
| 7,041,136 B2 | 5/2006 | Goble et al. | |

(56) References Cited

U.S. PATENT DOCUMENTS

| | | | |
|---|---|---|---|
| 7,063,701 B2 | 6/2006 | Michelson | |
| 7,063,702 B2 | 6/2006 | Michelson | |
| 7,066,961 B2 | 6/2006 | Michelson | |
| 7,074,237 B2 | 7/2006 | Goble et al. | |
| 7,090,698 B2 | 8/2006 | Goble et al. | |
| 7,094,239 B1 | 8/2006 | Michelson | |
| 7,105,024 B2 * | 9/2006 | Richelsoph | 623/17.13 |
| 7,112,206 B2 | 9/2006 | Michelson | |
| 7,118,579 B2 | 10/2006 | Michelson | |
| 7,118,598 B2 | 10/2006 | Michelson | |
| 7,128,760 B2 | 10/2006 | Michelson | |
| 7,128,761 B2 | 10/2006 | Kuras et al. | |
| 7,147,665 B1 * | 12/2006 | Bryan et al. | 623/17.16 |
| 7,163,561 B2 | 1/2007 | Michelson | |
| 7,175,662 B2 * | 2/2007 | Link et al. | 623/17.11 |
| 7,179,294 B2 | 2/2007 | Eisermann et al. | |
| 7,198,644 B2 * | 4/2007 | Schultz et al. | 623/17.15 |
| 7,204,852 B2 * | 4/2007 | Marnay et al. | 623/17.16 |
| 7,211,112 B2 | 5/2007 | Baynham et al. | |
| 7,217,291 B2 | 5/2007 | Zucherman et al. | |
| 7,217,292 B2 | 5/2007 | Ralph et al. | |
| 7,217,293 B2 | 5/2007 | Branch, Jr. | |
| 7,223,289 B2 | 5/2007 | Trieu et al. | |
| 7,232,463 B2 | 6/2007 | Falahee | |
| 7,232,464 B2 | 6/2007 | Mathieu et al. | |
| 7,326,248 B2 | 2/2008 | Michelson | |
| 7,326,250 B2 | 2/2008 | Beaurain et al. | |
| 7,410,501 B2 | 8/2008 | Michelson | |
| 7,431,735 B2 | 10/2008 | Liu et al. | |
| 7,435,262 B2 | 10/2008 | Michelson | |
| 7,442,209 B2 | 10/2008 | Michelson | |
| 7,445,635 B2 | 11/2008 | Fallin et al. | |
| 7,445,636 B2 | 11/2008 | Michelson | |
| 7,455,692 B2 | 11/2008 | Michelson | |
| 7,465,317 B2 | 12/2008 | Malberg et al. | |
| 7,481,840 B2 * | 1/2009 | Zucherman et al. | 623/17.15 |
| 7,494,507 B2 * | 2/2009 | Dixon et al. | 623/17.14 |
| 7,494,508 B2 * | 2/2009 | Zeegers | 623/17.15 |
| 7,503,933 B2 | 3/2009 | Michelson | |
| 7,517,363 B2 * | 4/2009 | Rogers et al. | 623/17.11 |
| 7,540,882 B2 | 6/2009 | Michelson | |
| 7,566,345 B1 | 7/2009 | Fallin et al. | |
| 7,575,599 B2 * | 8/2009 | Villiers et al. | 623/17.14 |
| 7,575,600 B2 * | 8/2009 | Zucherman et al. | 623/17.15 |
| 7,588,590 B2 | 9/2009 | Chervitz et al. | |
| 7,591,851 B2 | 9/2009 | Winslow et al. | |
| 7,594,932 B2 | 9/2009 | Aferzon et al. | |
| 7,601,170 B2 | 10/2009 | Winslow et al. | |
| 7,608,107 B2 | 10/2009 | Michelson | |
| 7,611,538 B2 * | 11/2009 | Belliard et al. | 623/17.15 |
| 7,618,453 B2 | 11/2009 | Goble et al. | |
| 7,618,455 B2 | 11/2009 | Goble et al. | |
| 7,618,456 B2 | 11/2009 | Mathieu et al. | |
| 7,621,955 B2 | 11/2009 | Goble et al. | |
| 7,621,956 B2 * | 11/2009 | Paul et al. | 623/17.15 |
| 7,621,958 B2 | 11/2009 | Zdeblick et al. | |
| 7,632,282 B2 | 12/2009 | Dinville | |
| 7,637,951 B2 | 12/2009 | Michelson | |
| 7,637,954 B2 | 12/2009 | Michelson | |
| 7,641,690 B2 | 1/2010 | Abdou | |
| 7,655,027 B2 | 2/2010 | Michelson | |
| 7,658,766 B2 | 2/2010 | Melkent et al. | |
| 7,682,396 B2 * | 3/2010 | Beaurain et al. | 623/17.14 |
| 7,695,516 B2 * | 4/2010 | Zeegers | 623/17.14 |
| 7,695,517 B2 | 4/2010 | Benzel et al. | |
| 7,708,776 B1 * | 5/2010 | Blain et al. | 623/17.14 |
| 7,717,959 B2 * | 5/2010 | William et al. | 623/17.15 |
| 7,727,280 B2 | 6/2010 | McLuen | |
| 7,749,252 B2 | 7/2010 | Zucherman et al. | |
| 7,749,274 B2 | 7/2010 | Razian | |
| 7,753,937 B2 | 7/2010 | Chervitz et al. | |
| 7,771,473 B2 | 8/2010 | Thramann | |
| 7,771,475 B2 | 8/2010 | Michelson | |
| 7,771,478 B2 | 8/2010 | Navarro et al. | |
| 7,776,090 B2 | 8/2010 | Winslow et al. | |
| 7,780,670 B2 | 8/2010 | Bonutti | |
| 7,789,914 B2 | 9/2010 | Michelson | |
| 7,794,502 B2 | 9/2010 | Michelson | |
| 7,799,053 B2 | 9/2010 | Haid, Jr. et al. | |
| 7,799,057 B2 | 9/2010 | Hudgins et al. | |
| 7,799,081 B2 | 9/2010 | McKinley | |
| 7,811,326 B2 | 10/2010 | Braddock, Jr. et al. | |
| 7,819,903 B2 | 10/2010 | Fraser et al. | |
| 7,824,445 B2 | 11/2010 | Biro et al. | |
| 7,833,255 B2 | 11/2010 | Chow et al. | |
| 7,842,088 B2 | 11/2010 | Rashbaum et al. | |
| 7,846,207 B2 | 12/2010 | Lechmann et al. | |
| 7,850,731 B2 | 12/2010 | Brittan et al. | |
| 7,850,732 B2 | 12/2010 | Heinz | |
| 7,850,733 B2 | 12/2010 | Baynham et al. | |
| 7,862,616 B2 | 1/2011 | Lechmann et al. | |
| 7,871,441 B2 | 1/2011 | Eckman | |
| 7,875,076 B2 | 1/2011 | Mathieu et al. | |
| 7,887,591 B2 | 2/2011 | Aebi et al. | |
| 7,892,261 B2 | 2/2011 | Bonutti | |
| 7,892,286 B2 | 2/2011 | Michelson | |
| 7,896,919 B2 * | 3/2011 | Belliard et al. | 623/17.15 |
| 7,909,871 B2 | 3/2011 | Abdou | |
| 7,914,560 B2 | 3/2011 | Hoy et al. | |
| 7,922,729 B2 | 4/2011 | Michelson | |
| 7,931,674 B2 | 4/2011 | Zucherman et al. | |
| 7,931,840 B2 | 4/2011 | Michelson | |
| 7,935,149 B2 | 5/2011 | Michelson | |
| 7,951,198 B2 | 5/2011 | Sucec et al. | |
| 7,955,390 B2 | 6/2011 | Fallin et al. | |
| 7,972,337 B2 | 7/2011 | Boyajian et al. | |
| 7,972,363 B2 | 7/2011 | Moskowitz et al. | |
| 7,972,365 B2 | 7/2011 | Michelson | |
| 7,976,566 B2 | 7/2011 | Michelson | |
| 7,985,255 B2 | 7/2011 | Bray et al. | |
| 7,985,258 B2 | 7/2011 | Zdeblick et al. | |
| 7,993,373 B2 | 8/2011 | Hoy et al. | |
| 7,998,177 B2 | 8/2011 | Hoy et al. | |
| 7,998,178 B2 | 8/2011 | Hoy et al. | |
| 7,998,211 B2 | 8/2011 | Baccelli et al. | |
| 8,002,835 B2 * | 8/2011 | Zeegers | 623/17.15 |
| 8,007,534 B2 | 8/2011 | Michelson | |
| 8,021,401 B2 | 9/2011 | Carl et al. | |
| 8,021,430 B2 | 9/2011 | Michelson | |
| 8,043,334 B2 | 10/2011 | Fisher et al. | |
| 8,062,336 B2 | 11/2011 | Triplett et al. | |
| 8,062,375 B2 | 11/2011 | Glerum et al. | |
| 8,066,741 B2 | 11/2011 | Fallin et al. | |
| 8,066,749 B2 | 11/2011 | Winslow et al. | |
| 8,070,816 B2 | 12/2011 | Taylor | |
| 8,070,819 B2 | 12/2011 | Aferzon et al. | |
| 8,075,593 B2 | 12/2011 | Hess | |
| 8,075,618 B2 | 12/2011 | Trieu et al. | |
| 8,075,621 B2 | 12/2011 | Michelson | |
| 8,114,082 B2 | 2/2012 | Boyajian et al. | |
| 8,257,439 B2 * | 9/2012 | Zeegers | 623/17.14 |
| 8,267,999 B2 * | 9/2012 | Beaurain et al. | 623/17.14 |
| 8,388,684 B2 * | 3/2013 | Bao et al. | 623/17.14 |
| 8,465,546 B2 | 6/2013 | Jodaitis et al. | |
| 8,685,100 B2 | 4/2014 | Jodaitis et al. | |
| 8,753,397 B2 | 6/2014 | Beaurain et al. | |
| 8,771,284 B2 | 7/2014 | Rashbaum et al. | |
| 8,858,635 B2 | 10/2014 | Hovorka et al. | |
| 2002/0035400 A1 * | 3/2002 | Bryan et al. | 623/17.15 |
| 2002/0040243 A1 | 4/2002 | Attali et al. | |
| 2002/0161444 A1 | 10/2002 | Choi | |
| 2002/0165613 A1 | 11/2002 | Lin et al. | |
| 2002/0193880 A1 | 12/2002 | Fraser | |
| 2003/0069586 A1 | 4/2003 | Errico et al. | |
| 2003/0074075 A1 | 4/2003 | Thomas, Jr. et al. | |
| 2003/0093153 A1 | 5/2003 | Banick et al. | |
| 2003/0093156 A1 | 5/2003 | Metzger et al. | |
| 2003/0135279 A1 | 7/2003 | Michelson | |
| 2003/0187436 A1 | 10/2003 | Bolger et al. | |
| 2003/0233145 A1 | 12/2003 | Landry et al. | |
| 2004/0010312 A1 | 1/2004 | Enayati | |
| 2004/0010316 A1 * | 1/2004 | William et al. | 623/17.16 |
| 2004/0024406 A1 | 2/2004 | Ralph et al. | |
| 2004/0083000 A1 * | 4/2004 | Keller et al. | 623/17.14 |

(56) References Cited

U.S. PATENT DOCUMENTS

| | | |
|---|---|---|
| 2004/0102846 A1* | 5/2004 | Keller et al. .............. 623/17.11 |
| 2004/0117022 A1* | 6/2004 | Marnay et al. ............ 623/17.16 |
| 2004/0133278 A1* | 7/2004 | Marino et al. ............ 623/17.14 |
| 2004/0133281 A1 | 7/2004 | Khandkar et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0210313 A1 | 10/2004 | Michelson |
| 2004/0225365 A1* | 11/2004 | Eisermann et al. ........ 623/17.15 |
| 2004/0243240 A1* | 12/2004 | Beaurain et al. ........... 623/17.14 |
| 2004/0254643 A1 | 12/2004 | Jackson |
| 2005/0015095 A1 | 1/2005 | Keller |
| 2005/0015149 A1 | 1/2005 | Michelson |
| 2005/0027363 A1* | 2/2005 | Gordon .................... 623/17.13 |
| 2005/0033428 A1 | 2/2005 | Keller |
| 2005/0033435 A1* | 2/2005 | Belliard et al. ............ 623/17.14 |
| 2005/0033437 A1* | 2/2005 | Bao et al. .................. 623/17.15 |
| 2005/0033438 A1* | 2/2005 | Schultz et al. ............ 623/17.15 |
| 2005/0038512 A1 | 2/2005 | Michelson |
| 2005/0038516 A1* | 2/2005 | Spoonamore ............. 623/17.14 |
| 2005/0043800 A1* | 2/2005 | Paul et al. ................. 623/17.15 |
| 2005/0043804 A1* | 2/2005 | Gordon et al. ............ 623/17.16 |
| 2005/0049590 A1 | 3/2005 | Alleyne et al. |
| 2005/0060034 A1* | 3/2005 | Berry et al. ............... 623/17.11 |
| 2005/0060037 A1 | 3/2005 | Michelson |
| 2005/0065608 A1 | 3/2005 | Michelson |
| 2005/0065611 A1* | 3/2005 | Huppert et al. ........... 623/17.15 |
| 2005/0085917 A1* | 4/2005 | Marnay et al. ............ 623/17.16 |
| 2005/0131544 A1 | 6/2005 | Kuras et al. |
| 2005/0143733 A1 | 6/2005 | Petit |
| 2005/0149189 A1* | 7/2005 | Mokhtar et al. .......... 623/17.11 |
| 2005/0154462 A1* | 7/2005 | Zucherman et al. ....... 623/17.15 |
| 2005/0165485 A1* | 7/2005 | Trieu ....................... 623/17.13 |
| 2005/0197705 A1* | 9/2005 | Arnin et al. ............... 623/17.15 |
| 2005/0197706 A1* | 9/2005 | Hovorka et al. ........... 623/17.15 |
| 2005/0216086 A1* | 9/2005 | Marik et al. .............. 623/17.15 |
| 2005/0246024 A1* | 11/2005 | Zeegers ................... 623/17.15 |
| 2005/0256579 A1* | 11/2005 | Keller et al. .............. 623/17.15 |
| 2005/0267581 A1* | 12/2005 | Marnay et al. ............ 623/17.14 |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1* | 12/2005 | Zucherman et al. ....... 623/17.15 |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0016768 A1 | 1/2006 | Grichar et al. |
| 2006/0020341 A1* | 1/2006 | Schneid et al. ........... 623/17.14 |
| 2006/0036261 A1 | 2/2006 | McDonnell |
| 2006/0036325 A1* | 2/2006 | Paul et al. ................. 623/17.14 |
| 2006/0036326 A1* | 2/2006 | Baumgartner et al. .... 623/17.15 |
| 2006/0041314 A1* | 2/2006 | Millard ..................... 623/17.16 |
| 2006/0058878 A1 | 3/2006 | Michelson |
| 2006/0069437 A1* | 3/2006 | Weber ...................... 623/17.14 |
| 2006/0085076 A1 | 4/2006 | Krishna et al. |
| 2006/0085077 A1 | 4/2006 | Cook et al. |
| 2006/0095136 A1 | 5/2006 | McLuen |
| 2006/0111783 A1* | 5/2006 | Aflatoon et al. .......... 623/17.14 |
| 2006/0116768 A1* | 6/2006 | Krueger et al. ........... 623/17.14 |
| 2006/0116769 A1* | 6/2006 | Marnay et al. ............ 623/17.15 |
| 2006/0122703 A1* | 6/2006 | Aebi et al. ................ 623/17.15 |
| 2006/0129244 A1 | 6/2006 | Ensign |
| 2006/0136063 A1* | 6/2006 | Zeegers ................... 623/17.14 |
| 2006/0149371 A1* | 7/2006 | Marik et al. .............. 623/17.11 |
| 2006/0149378 A1* | 7/2006 | Chase et al. .............. 623/17.11 |
| 2006/0155377 A1* | 7/2006 | Beaurain et al. .......... 623/17.14 |
| 2006/0190082 A1* | 8/2006 | Keller et al. .............. 623/17.11 |
| 2006/0206208 A1 | 9/2006 | Michelson |
| 2006/0235526 A1* | 10/2006 | Lemaire .................... 623/17.14 |
| 2006/0241764 A1 | 10/2006 | Michelson |
| 2006/0253201 A1 | 11/2006 | McLuen |
| 2006/0259147 A1* | 11/2006 | Krishna et al. ............ 623/17.15 |
| 2007/0010886 A1 | 1/2007 | Banick et al. |
| 2007/0016297 A1 | 1/2007 | Johnson |
| 2007/0032871 A1 | 2/2007 | Michelson |
| 2007/0073404 A1* | 3/2007 | Rashbaum et al. ........ 623/17.14 |
| 2007/0100454 A1* | 5/2007 | Burgess et al. ........... 623/17.14 |
| 2007/0118223 A1* | 5/2007 | Allard et al. .............. 623/17.13 |
| 2007/0123985 A1 | 5/2007 | Errico et al. |
| 2007/0162137 A1 | 7/2007 | Kloss et al. |
| 2007/0250167 A1 | 10/2007 | Bray et al. |
| 2007/0250168 A1* | 10/2007 | Lechmann et al. ........ 623/17.11 |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0027547 A1 | 1/2008 | Yu et al. |
| 2008/0027550 A1 | 1/2008 | Link et al. |
| 2008/0033555 A1* | 2/2008 | Link et al. ................. 623/17.15 |
| 2008/0033562 A1 | 2/2008 | Krishna et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |

(56) References Cited

U.S. PATENT DOCUMENTS

| | | |
|---|---|---|
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0053693 A1 | 3/2012 | Zeegers |
| 2012/0116466 A1 | 5/2012 | Dinville et al. |
| 2012/0330424 A1 | 12/2012 | Zeegers |
| 2013/0013006 A1 | 1/2013 | Rashbaum et al. |
| 2013/0150968 A1 | 6/2013 | Dinville et al. |
| 2013/0166029 A1 | 6/2013 | Dinville et al. |
| 2013/0253648 A1 | 9/2013 | Beaurain et al. |
| 2013/0253651 A1 | 9/2013 | Dinville |
| 2013/0282124 A1 | 10/2013 | Jodaitis et al. |
| 2014/0114413 A1 | 4/2014 | Allain et al. |

FOREIGN PATENT DOCUMENTS

| | | |
|---|---|---|
| DE | 4328690 | 3/1995 |
| DE | 29911422 | 8/1999 |
| DE | 20320454 | 10/2004 |
| DE | 10323363 | 12/2004 |
| EP | 0637439 | 2/1995 |
| EP | 0697200 | 2/1996 |
| EP | 0951879 | 10/1999 |
| EP | 1222903 | 7/2002 |
| EP | 1287795 | 3/2003 |
| EP | 1504733 | 2/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2916956 | 12/2008 |
| WO | WO9515133 | 6/1995 |
| WO | WO9817209 | 4/1998 |
| WO | WO9956676 | 11/1999 |
| WO | WO0143620 | 6/2001 |
| WO | WO0213732 | 2/2002 |
| WO | WO02058599 | 8/2002 |
| WO | WO03005939 | 1/2003 |
| WO | WO03026522 | 4/2003 |
| WO | WO03099172 | 12/2003 |
| WO | WO2004034935 | 4/2004 |
| WO | WO2004039291 | 5/2004 |
| WO | WO2004071360 | 8/2004 |
| WO | WO2004089256 | 10/2004 |
| WO | WO2005007040 | 1/2005 |
| WO | WO2005007044 | 1/2005 |
| WO | WO2005051243 | 6/2005 |
| WO | WO2005063150 | 7/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006130460 | 12/2006 |
| WO | WO2007000654 | 1/2007 |
| WO | WO2007034310 | 3/2007 |
| WO | WO2007063398 | 6/2007 |
| WO | WO2007078978 | 7/2007 |
| WO | WO2008099277 | 8/2008 |
| WO | WO2008149223 | 12/2008 |
| WO | WO2009033100 | 3/2009 |
| WO | WO2011080535 | 7/2011 |
| WO | WO2013124453 | 8/2013 |

OTHER PUBLICATIONS

World Intellectual Property Organization; International Preliminary Report on Patentability for PCT Pub'n. No. WO2005104996, App'n. No. PCT/IB2005/01151; Jun. 28, 2006; WIPO; Geneva, Switzerland; all pages.

European Patent Office; search report in Application No. 10185004, Pub. No. EP2327375; Apr. 6, 2011; European Patent Office; Munich, Germany; All Pages.

European Patent Office; search report in Application No. 13170071, Pub. No. EP2633835; Oct. 1, 2013; European Patent Office; Munich, Germany; All Pages.

World Intellectual Property Organization; Written Opinion of the International Searching Authority for PCT Pub'n. No. WO2005074839, App'n. No. PCT/IB2005/00280; Jun. 24, 2005; WIPO; Geneva, Switzerland; all pages.

World Intellectual Property Organization; International Preliminary Report on Patentability for PCT Pub'n. No. WO2005074839, App'n. No. PCT/IB2005/00280; Jan. 16, 2006; WIPO; Geneva, Switzerland; all pages.

European Patent Office; Office Action for Pub'n. No. EP1711133, App'n. No. EP050702425; Mar. 2, 2009; EPO; Munich, Germany; all pages.

LDR Medical, by its attorneys; Reply to Office Action for Pub'n. No. EP1711133, App'n. No. EP050702425; Jul. 22, 2009; EPO; Munich, Germany; all pages.

European Patent Office; Notice of Intention to Grant a European Patent for Pub'n. No. EP1711133, App'n. No. EP050702425; Oct. 22, 2010; EPO; Munich, Germany; all pages.

National Institute of Industrial Property (France); Search Report for Pub'n. No. FR2879436, App. No. FR0413728; Aug. 11, 2005; National Institute of Industrial Property (France); France; all pages.

World Intellectual Property Organization; International Search Report and Written Opinion of the International Searching Authority for PCT Pub'n No. WO2006120505, App. No. PCT/IB2005/004093; Aug. 30, 2006; WIPO; Geneva, Switzerland; all pages.

LDR Medical, by its attorneys; Chapter II amendments for PCT Pub'n No. WO2006120505, App. No. PCT/IB2005/004093; Oct. 30, 2006; WIPO; Geneva, Switzerland; all pages.

World Intellectual Property Oganization; International Preliminary Report on Patentability for PCT Pub'n No. WO2006120505, App. No. PCT/IB2005/004093; Feb. 22, 2007; WIPO; Geneva, Switzerland; all pages.

European Patent Office; Office action and Search report in Application No. 05857774, Pub. No. EP1845903; May 6, 2009; European Patent Office; Munich, Germany; All Pages.

LDR Medical, by its attorneys; Amendments and Reply in European Patent Application No. 05857774, Pub. No. EP1845903; Nov. 13, 2009; European Patent Office; Munich, Germany; All Pages.

European Patent Office; Office action and search report in Application No. 05857774, Pub. No. EP1845903; Apr. 11, 2011; European Patent Office; Munich, Germany; All Pages.

European Patent Office; Office action and search report in Application No. 11165170, Pub. No. EP2363080; Jul. 21, 2011; European Patent Office; Munich, Germany; All Pages.

(56) References Cited

OTHER PUBLICATIONS

LDR Medical, by its attorneys; Amendments and Reply in European Patent Application No. 05857774, Pub. No. EP1845903; Oct. 11, 2011; European Patent Office; Munich, Germany; All Pages.
LDR Medical, by its attorneys; Amendments and Reply in European Patent Application No. 11165170, Pub. No. EP2363080; Mar. 6, 2012; European Patent Office; Munich, Germany; All Pages.
European Patent Office; Office action in Application No. 11165170, Pub. No. EP2363080; May 15, 2012; European Patent Office; Munich, Germany; All Pages.
National Institute of Industrial Property (France); Preliminary Search Report in French Pub. No. FR2887762, App'n No. FR0506652; Dec. 21, 2005; National Institute of Industrial Property (France); France; all pages.
World Intellectual Property Organization; International Search Report for PCT Pub'n No. WO2007000654, App'n No. PCT/IB2006/01781; Mar. 14, 2007; WIPO; Geneva, Switzerland; all pages.
World Intellectual Property Organization; Written Opinion of the International Searching Authority for PCT Pub'n No. WO2007000654, App'n No. PCT/IB2006/01781; Mar. 14, 2007; WIPO; Geneva, Switzerland; all pages.
World Intellectual Property Organization; International Preliminary Report on Patentability for PCT Pub'n No. WO2007000654, App'n No. PCT/IB2006/01781; Jul. 19, 2007; WIPO; Geneva, Switzerland; all pages.
National Institute of Industrial Property (France); Preliminary Search Report in French Pub. No. FR2891135, App'n No. FR0509740; Jun. 27, 2006; National Institute of Industrial Property (France); France; all pages.
World Intellectual Property Organization; International Search Report for PCT Pub'n No. WO2007034310, App'n No. PCT/IP/006/02632; Feb. 13, 2007; WIPO; Geneva, Switzerland; all pages.
World Intellectual Property Organization; Written Opinion of the International Searching Authority for PCT Pub'n No. WO2007034310, App'n No. PCT/IP/006/02632; Feb. 13, 2007; WIPO; Geneva, Switzerland; all pages.
World Intellectual Property Organization; International Preliminary Report on Patentability for PCT Pub'n No. WO2007034310, App'n No. PCT/IP/006/02632; Aug. 14, 2007; WIPO; Geneva, Switzerland; all pages.
National Institute of Industrial Property (France); Preliminary Search Report in French Pub. No. FR2893838, App'n No. FR0512133; Aug. 4, 2006; National Institute of Industrial Property (France); France; all pages.
World Intellectual Property Organization; International Search Report for PCT Pub'n No. WO2007063398, App'n No. PCT/IB2006/03418; Jul. 13, 2007; WIPO; Geneva, Switzerland; all pages.
World Intellectual Property Organization; Written Opinion of the International Searching Authority for PCT Pub'n No. WO2007063398, App'n No. PCT/IB2006/03418; Jul. 13, 2007; WIPO; Geneva, Switzerland; all pages.
World Intellectual Property Organization; International Preliminary Report on Patentability for PCT Pub'n No. WO2007063398, App'n No. PCT/IB2006/03418; Nov. 12, 2007; WIPO; Geneva, Switzerland; all pages.
World Intellectual Property Organization; International Search Report for PCT Pub'n No. WO2008099277, App'n No. PCT/IB2008/00349; Nov. 7, 2008; WIPO; Geneva, Switzerland; all pages.
World Intellectual Property Organization; Written Opinion of the International Searching Authority for PCT Pub'n No. WO2008099277, App'n No. PCT/IB2008/00349; Nov. 7, 2008; WIPO; Geneva, Switzerland; all pages.
World Intellectual Property Organization; International Preliminary Report on Patentability for PCT Pub'n No. WO2008099277, App'n No. PCT/IB2008/00349; May 29, 2009; WIPO; Geneva, Switzerland; all pages.
U.S. Patent & Trademark Office; Notice of Allowance in U.S. Appl. No. 10/476,565; Nov. 29, 2007; USPTO; Alexandria, Virgina; All Pages.
LDR Medical, by its attorneys; Amendment After Final in U.S. Appl. No. 10/476,565; Nov. 29, 2007; USPTO; Alexandria, Virgina; All Pages.
LDR Medical, by its attorneys; Reply to Office Action in U.S. Appl. No. 10/476,565; Nov. 6, 2007; USPTO; Alexandria, Virgina; All Pages.
U.S. Patent & Trademark Office; Office Action in U.S. Appl. No. 10/476,565; May 7, 2007; USPTO; Alexandria, Virgina; All Pages.
LDR Medical, by its attorneys; Reply to Office Action in U.S. Appl. No. 10/476,565; Jan. 18, 2007; USPTO; Alexandria, Virgina; All Pages.
U.S. Patent & Trademark Office; Office Action in U.S. Appl. No. 10/476,565; Jul. 18, 2006; USPTO; Alexandria, Virgina; All Pages.
U.S. Patent & Trademark Office; Office Action in U.S. Appl. No. 12/025,677; Nov. 7, 2014, USPTO; Alexandria, Virginia; All Pages.
U.S. Patent & Trademark Office; Reply to Office Action in U.S. Appl. No. 12/025,677; Aug. 19, 2014; Alexandria, Virginia; All Pages.
U.S. Patent & Trademark Office; Reply to Office Action in U.S. Appl. No. 12/025,677; Feb. 19, 2014; USPTO; Alexandria, Virginia; All Pages.
LDR Medical, by its Attorneys; Reply to Office Action in U.S. Appl. No. 12/025,677; Dec. 20, 2013; USPTO; Alexandria, Virginia; All Pages.
U.S. Patent & Trademark Office; Office Action in U.S. Appl. No. 12/025,677; Jun. 20, 2013; USPTO; Alexandria, Virginia; All Pages.
LDR Medical, by its attorneys; Reply to Office Action In U.S. Appl. No. 12/025,677; Dec. 29, 2012; USPTO; Alexandria, Virginia; All Pages.
U.S. Patent & Trademark Office; Office Action in U.S. Appl. No. 12/025,677; Jun. 29, 2012; USPTO; Alexandria, Virgina; All Pages.
LDR Medical, by its attorneys; Reply to Office Action in U.S. Appl. No. 12/025,677; Apr. 9, 2012; USPTO; Alexandria, Virgina; All Pages.
U.S. Patent & Trademark Office; Office Action in U.S. Appl. No. 12/025,677; Oct. 7, 2011; USPTO; Alexandria, Virginia; All Pages.
U.S. Patent & Trademark Office; Notice of Allowance in U.S. Appl. No. 10/494,418; Sep. 20, 2005; USPTO; Alexandria, Virgina; All Pages.
U.S. Patent & Trademark Office; Notice of Allowance in U.S. Appl. No. 10/533,846; Nov. 4, 2009; USPTO; Alexandria, Virgina; All Pages.
U.S. Patent & Trademark Office; Notice of Allowance in U.S. Appl. No. 12/424,364; Aug. 2, 2012; USPTO; Alexandria, Virgina; All Pages.
U.S. Patent & Trademark Office; Notice of Allowance in U.S. Appl. No. 12/424,364; Jul. 24, 2012; USPTO; Alexandria, Virgina; All Pages.
LDR Medical, by its attorneys; Reply to Office Action in U.S. Appl. No. 12/424,364; Jul. 6, 2012; USPTO; Alexandria, Virginia; All Pages.
U.S. Patent & Trademark Office; Office Action in U.S. Appl. No. 12/424,364; May 23, 2012; USPTO; Alexandria, Virginia; All Pages.
LDR Medical, by its attorneys; Interview Summary and Terminal Disclaimer in U.S. Appl. No. 12/424,364; May 2, 2012; USPTO; Alexandria, Virginia; All Pages.
LDR Medical, by its attorneys; Reply to Office Action in U.S. Appl. No. 12/424,364; Feb. 27, 2012; USPTO; Alexandria, Virginia; All Pages.
U.S. Patent & Trademark Office; Office Action in U.S. Appl. No. 12/424,364; Jan. 26, 2012; USPTO; Alexandria, Virginia; All Pages.
LDR Medical, by its attorneys; Reply to Office Action in U.S. Appl. No. 12/424,364; Nov. 18, 2011; USPTO; Alexandria, Virginia; All Pages.
U.S. Patent & Trademark Office; Office Action in U.S. Appl. No. 12/424,364; May 18, 2011; USPTO; Alexandria, Virgina; All Pages.
U.S. Patent & Trademark Office; Notice of Allowance in U.S. Appl. No. 13/616,448; Feb. 7, 2014; USPTO; Alexandria, Virginia; All Pages.
U.S. Patent & Trademark Office; Office Action in U.S. Appl. No. 13/616,448; Aug. 22, 2013; USPTO; Alexandria, Virginia; All Pages.
U.S. Patent & Trademark Office; Office Action in U.S. Appl. No. 14/306,785; Oct. 22, 2014; USPTO; Alexandria, Virgina; All Pages.

(56) References Cited

OTHER PUBLICATIONS

U.S. Patent & Trademark Office; Notice of allowance in U.S. Appl. No. 11/051,710; Jun. 11, 2014; USPTO; Alexandria, Virgina; All Pages.
LDR Medical, by its attorneys; Request for Continued Examination in U.S. Appl. No. 11/051,710; Jul. 11, 2013; USPTO; Alexandria, Virgina; All Pages.
U.S. Patent & Trademark Office; Notice of Allowance in U.S. Appl. No. 11/051,710; Apr. 11, 2013; USPTO; Alexandria, Virgina; All Pages.
LDR Medical, by its attorneys; Appeal Brief in U.S. Appl. No. 11/051,710; Jan. 15, 2013; USPTO, Alexandria, Virginia; All Pages.
U.S Patent & Trademark Office; Office Action in U.S. Appl. No. 11/051,710; Dec. 15, 2011; UPSTO; Alexandria, Virginia; All Pages.
LDR Medical, by its attorneys, Reply to Office Action in U.S. Appl. No. 11/051,710; Oct. 11, 2011; USPTO; Alexandria, Virginia; All Pages.
U.S. Patent & Trademark Office; Office Action in U.S. Appl. No. 11/051,710; Apr. 11, 2011; USPTO; Alexandria, Virginia; All Pages.
LDR Medical, by its attorneys; Reply to Office Action in U.S. Appl. No. 11/051,710; Jan. 20, 2011; USPTO; Alexandria, Virginia; All Pages.
U.S. Patent & Trademark Office; Office Action in U.S. Appl. No. 11/051,710; Jul. 20, 2010; USPTO; Alexandria, Virgina; All Pages.
LDR Medical, by its attorneys; Reply to Office Action in U.S. Appl. No. 11/051,710; Apr. 26, 2010; USPTO; Alexandria, Virgina; All Pages.
U.S. Patent & Trademark Office; Office Action in U.S. Appl. No. 11/051,710; Oct. 26, 2009; USPTO; Alexandria, Virgina; All Pages.
U.S. Patent & Trademark Office; Notice of Allowance in U.S. Appl. No. 11/109,276; Dec. 8, 2009; USPTO; Alexandria, Virgina; All Pages.
U.S. Patent & Trademark Office; Notice of Allowance in U.S. Appl. No. 12/360,050; Aug. 2, 2012; USPTO; Alexandria, Virgina; All Pages.
U.S. Patent & Trademark Office; Notice of Allowance in U.S. Appl. No. 12/360,050; Jul. 6, 2012; USPTO; Alexandria, Virgina; All Pages.
U.S. Patent & Trademark Office; Notice of Allowance in U.S. Appl. No. 12/360,050; May 18, 2012; USPTO; Alexandria, Virgina; All Pages.
U.S. Patent & Trademark Office; Notice of Allowance in U.S. Appl. No. 12/360,050; Mar. 26, 2012; USPTO; Alexandria, Virgina; All Pages.
LDR Medical, by its attorneys; Reply to Office Action in U.S. Appl. No. 12/360,050; Mar. 6, 2012; USPTO; Alexandria, Virginia; All Pages.
U.S. Patent & Trademark Office Action in U.S. Appl. No. 12/360,050; Sep. 6, 2011; USPTO, Alexandria, Virginia; All Pages.
LDR Medical, by its attorneys, Reply to Office Action in U.S. Appl. No. 12/600,050; Jun. 16, 2011; USPTO; Alexandria, Virginia; All Pages.
U.S. Patent & Trademark Office; Office Action in U.S. Appl. No. 12/360,050; Dec. 17, 2010; USPTO; Alexandria, Virginia; All Pages.
U.S. Patent & Trademark Office; Office Action in U.S. Appl. No. 13/603,043; Jul. 24, 2014; USPTO; Alexandria, Virginia; All Pages.
LDR Medical, by its attorneys; Reply to Office Action in U.S. Appl. No. 13/603,043; May 21, 2014; USPTO; Alexandria, Virginia; All Pages.
U.S. Patent & Trademark Office; Office Action in U.S. Appl. No. 13/603,043; Nov. 21, 2013; USPTO; Alexandria, Virginia; All Pages.
LDR Medical, by its attorneys; Reply to Office Action in U.S. Appl. No. 13/603,043; Oct. 9, 2013; USPTO; Alexandria, Virgina; All Pages.
U.S. Patent & Trademark Office; Office Action in U.S. Appl. No. 13/603,043; Apr. 9, 2013; USPTO; Alexandria, Virgina; All Pages.
U.S. Patent & Trademark Office; Notice of Allowance in U.S. Appl. No. 11/180,868; Jul. 31, 2009; USPTO; Alexandria, Virgina; All Pages.

U.S. Patent & Trademark Office; Notice of Allowance in U.S. Appl. No. 11/180,868; Jul. 17, 2009; USPTO; Alexandria, Virgina; All Pages.
U.S. Patent & Trademark Office; Notice of Allowance in U.S. Appl. No. 12/435,955; Jan. 16, 2013; USPTO; Alexandria, Virgina; All Pages.
LDR Medical, by its attorneys; Reply to Office Action in U.S. Appl. No. 12/435,955; Dec. 24, 2012; USPTO; Alexandria, Virgina; All Pages.
U.S. Patent & Trademark Office, Office Action in U.S. Appl. No. 12/435,955; Jul. 23, 2012; USPTO; Alexandria, Virginia; All Pages.
LDR Medical, by its attorneys; Reply to Office Action in U.S. Appl. No. 12/435,955; Apr. 11, 2012; USPTO; Alexandria, Virginia; All Pages.
U.S. Patent & Trademark Office; Office Action in U.S. Appl. No. 12/435,955; Oct. 11, 2011; USPTO; Alexandria, Virginia; All Pages.
U.S. Patent & Trademark Office; Office Action in U.S. Appl. No. 13/892,933; Jul. 28, 2014; USPTO; Alexandria, Virginia; All Pages.
LDR Medical, by its attorneys; Reply to Office Action in U.S. Appl. No. 13/892,933; Apr. 2, 2014; USPTO; Alexandria, Virginia; All Pages.
U.S. Patent & Trademark Office; Office Action in U.S. Appl. No. 13/892,933; Jan. 2, 2014; USPTO; Alexandria, Virgina; All Pages.
U.S. Patent & Trademark Office; Notice of Allowance in U.S. Appl. No. 11/341,007; Jul. 26, 2010; USPTO; Alexandria, Virgina; All Pages.
LDR Medical, by its attorneys; Reply to Office Action in U.S. Appl. No. 11/341,007; Jun. 17, 2010; USPTO; Alexandria, Virginia; All Pages.
U.S. Patent & Trademark Office; Office Action in U.S. Appl. No. 11/341,007; Dec. 17, 2009; USPTO; Alexandria, Virgina; All Pages.
LDR Medical, by its attorneys; Reply to Office Action in U.S. Appl. No. 11/341,007; Oct. 13, 2009; USPTO; Alexandria, Virginia; All Pages.
U.S. Patent & Trademark Office; Office Action in U.S. Appl. No. 11/341,007; Apr. 13, 2009; USPTO; Alexandria, Virginia; All Pages.
U.S. Patent & Trademark Office; Notice of Allowance in Application U.S. Appl. No. 12/955,898; Aug. 8, 2014; USPTO; Alexandria, Virginia; All Pages.
LDR Medical, by its attorneys; Reply to Office Action in U.S. Appl. No. 12/955,898; Aug. 4, 2014; USPTO; Alexandria, Virgina; All Pages.
U.S. Patent & Trademark Office; Office Action in U.S. Appl. No. 12/955,898; Mar. 3, 2014; USPTO; Alexandria, Virgina; All Pages.
LDR Medical, by its attorneys; Reply to Office Action in U.S. Appl. No. 12/955,898; Jul. 10, 2013; USPTO; Alexandria, Virginia; All Pages.
U.S. Patent & Trademark Office; Office Action in U.S. Appl. No. 12/955,898; Jan. 10, 2013; USPTO; Alexandria, Virginia; All Pages.
LDR Medical, by its attorneys; Reply to Office Action in U.S. Appl. No. 12/955,898; Dec. 3, 2012; USPTO; Alexandria, Virginia; All Pages.
U.S. Patent & Trademark Office; Office Action in U.S. Appl. No. 12/955,898; Jun. 1, 2012; USPTO; Alexandria, Virginia; All Pages.
LDR Medical, by its attorneys; Reply to Office Action in U.S. Appl. No. 12/955,898; Mar. 19, 2012; USPTO; Alexandria, Virginia; All Pages.
U.S. Patent & Trademark Office; Office Action in U.S. Appl. No. 12/955,898; Mar. 19, 2012; USPTO; Alexandria, Virginia; All Pages.
LDR Medical, by its attorneys; Reply Brief in U.S. Appl. No. 11/362,253; Aug. 20, 2012; USPTO; Alexandria, Virginia, All Pages.
U.S. Patent & Trademark Office; Examiners Answer to Appeal Brief in U.S. Appl. No. 11/362,253; Jun. 20, 2012; USPTO; Alexandria, Virgina; All Pages.
LDR Medical, by its attorneys; Appeal Brief in U.S. Appl. No. 11/362,253; Apr. 9, 2012; USPTO; Alexandria, Virginia; All Pages.
U.S. Patent & Trademark Office; Office Action in U.S. Appl. No. 11/362,253; Mar. 8, 2011; USPTO; Alexandria, Virginia; All Pages.
LDR Medical, by its attorneys; Reply to Office Action in U.S. Appl. No. 11/362,253; Dec. 20, 2010; USPTO; Alexandria, Virginia; All Pages.
U.S. Patent & Trademark Office; Office Action in U.S. Appl. No. 11/362,253; Jun. 18, 2010; USPTO; Alexandria, Virgina; All Pages.

(56) References Cited

OTHER PUBLICATIONS

LDR Medical, by its attorneys; Reply to Office Action in U.S. Appl. No. 11/362,253; Apr. 15, 2010; USPTO; Alexandria, Virgina; All Pages.
U.S. Patent & Trademark Office; Office Action in U.S. Appl. No. 11/362,253; Oct. 15, 2009; USPTO; Alexandria, Virgina; All Pages.
LDR Medical, by its attorneys; Reply to Office Action in U.S. Appl. No. 11/362,253; Aug. 18, 2009; USPTO; Alexandria, Virginia; All Pages.
U.S. Patent & Trademark Office; Office Action in U.S. Appl. No. 11/362,253; Feb. 18, 2009; USPTO; Alexandria, Virginia; All Pages.
U.S. Patent & Trademark Office; Notice of Allowance in U.S. Appl. No. 13/620,797; Jan. 29, 2014; USPTO; Alexandria, Virginia; All Pages.
LDR Medical, by its attorneys; Reply to Office Action in U.S. Appl. No. 13/620,797; Nov. 5, 2013; USPTO; Alexandria, Virginia; All Pages.
U.S. Patent & Trademark Office; Office Action in U.S. Appl. No. 13/620,797; Jul. 5, 2013; USPTO; Alexandria, Virginia; All Pages.
U.S. Patent & Trademark Office; Notice of Allowance in U.S. Appl. No. 12/134,884; Nov. 1, 2012; USPTO; Alexandria, Virginia; All Pages.
LDR Medical, by its attorneys; Reply to Office Action in U.S. Appl. No. 12/134,884; Jul. 31, 2012; USPTO; Alexandria, Virginia; All Pages.
U.S. Patent & Trademark Office; Office Action in U.S. Appl. No. 12/134,884; Jan. 31, 2012; USPTO; Alexandria, Virgina; All Pages.
U.S. Patent & Trademark Office; Office Action in U.S. Appl. No. 13/732,244; Sep. 19, 2014; USPTO; Alexandria, Virginia; All Pages.
LDR Medical, by its attorneys; Reply to Office Action in U.S. Appl. No. 13/732,244; Jul. 30, 2014; USPTO; Alexandria, Virgina; All Pages.
U.S. Patent & Trademark Office; Office Action in U.S. Appl. No. 13/732,244; Apr. 30, 2014; USPTO; Alexandria, Virgina; All Pages.
U.S. Patent & Trademark Office; Notice of Allowance in U.S. Appl. No. 11/676,237; Feb. 20, 2013; USPTO; Alexandria, Virgina; All Pages.
LDR Medical, by its attorneys; Reply to Office Action in U.S. Appl. No. 11/676,237; Feb. 6, 2013; USPTO; Alexandria, Virgina; All Pages.
U.S. Patent & Trademark Office; Office Action in U.S. Appl. No. 11/676,237; Nov. 6, 2012; USPTO; Alexandria, Virginia; All Pages.
LDR Medical, by its attorneys; Reply to Office Action in U.S. Appl. No. 11/676,237; Jul. 16, 2012; USPTO; Alexandria, Virginia; All Pages.
U.S. Patent & Trademark Office; Office Action in U.S. Appl. No. 11/676,237; Feb. 16, 2012; USPTO; Alexandria, Virginia; All Pages.
LDR Medical, by its attorneys; Appeal Brief in U.S. Appl. No. 11/676,237; Oct. 17, 2011; USPTO; Alexandria, Virginia; All Pages.
U.S. Patent & Trademark Office; Office Action in U.S. Appl. No. 11/676,237; Sep. 15, 2010; USPTO; Alexandria, Virginia; All Pages.
LDR Medical, by its attorneys; Reply to Office Action in U.S. Appl. No. 11/676,237; Jun. 18, 2010; USPTO; Alexandria, Virgina; All Pages.
U.S. Patent & Trademark Office; Office Action in U.S. Appl. No. 11/676,237; Dec. 18, 2009; USPTO; Alexandria, Virgina; All Pages.
LDR Medical, by its attorneys; Reply to Office Action in U.S. Appl. No. 11/676,237; Sep. 21, 2009; USPTO; Alexandria, Virgina; All Pages.
U.S. Patent & Trademark Office; Office Action in U.S. Appl. No. 11/676,237; Mar. 20, 2009; USPTO; Alexandria, Virgina; All Pages.
U.S. Patent & Trademark Office; Office Action in U.S. Appl. No. 13/919,704; Jun. 2, 2014; USPTO; Alexandria, Virgina; All Pages.
LDR Medical, by its attorneys; Reply to Office Action in U.S. Appl. No. 13/919,704; Jan. 31, 2014; USPTO; Alexandria, Virgina; All Pages.
U.S. Patent & Trademark Office; Office Action in U.S. Appl. No. 13/919,704; Oct. 31, 2013; USPTO; Alexandria, Virgina; All Pages.
LDR Medical, by its attorneys; Interview Summary in U.S. Appl. No. 12/527,373; Jan. 31, 2014; USPTO; Alexandria, Virgina; All Pages.
U.S. Patent & Trademark Office; Notice of Allowance in U.S. Appl. No. 12/527,373; Dec. 24, 2013; USPTO; Alexandria, Virgina; All Pages.
LDR Medical, by its attorneys; Request for Continued Examination in U.S. Appl. No. 12/527,373; Dec. 2, 2013; USPTO; Alexandria, Virgina; All Pages.
U.S. Patent & Trademark Office; Notice of Allowance in U.S. Appl. No. 12/527,373; Aug. 30, 2013; USPTO; Alexandria, Virgina; All Pages.
U.S. Patent & Trademark Office; Interview Summary in U.S. Appl. No. 12/527,373; Aug. 30, 2013; USPTO; Alexandria, Virgina; All Pages.
LDR Medical, by its attorneys; Appeal Brief in U.S. Appl. No. 12/527,373; Apr. 24, 2013; USPTO; Alexandria, Virgina; All Pages.
U.S. Patent & Trademark Office; Office Action in U.S. Appl. No. 12/527,373; Sep. 24, 2012; USPTO; Alexandria, Virginia; All Pages.
LDR Medical, by its attorneys; Reply to Office Action in U.S. Appl. No. 12/527,373; Jun. 21, 2012; USPTO; Alexandria, Virgina; All Pages.
U.S. Patent & Trademark Office; Office Action in U.S. Appl. No. 12/527,373; Dec. 21, 2011; USPTO; Alexandria, Virgina; All Pages.

\* cited by examiner

INTERVERTEBRAL DISC PROSTHESIS

CROSS REFERENCE TO RELATED APPLICATIONS

This application is a continuation of application Ser. No. 12/391,086 filed Feb. 23, 2009, and issuing as U.S. Pat. No. 8,002,835 on Aug. 23, 2011, which is a continuation of application Ser. No. 11/098,266 filed Apr. 4, 2005, and issuing as U.S. Pat. No. 7,494,508 on Feb. 24, 2009. This application claims priority under 35 U.S.C. 119 to French Patent Application No. 04 04501, filed in FRANCE on Apr. 28, 2004.

BACKGROUND

The present invention relates to an intervertebral disc prosthesis, intended to be substituted for fibro-cartilaginous discs ensuring a bond between the vertebrae of the spinal column.

Various types of intervertebral disc prostheses are known in the prior art. Numerous prostheses, such as for example in the patent application FR 2 846 550 and WO 02 089 701, are constituted in a lower plate and an upper plate forming a sort of cage around a central core. A part of these prostheses enables the upper plate to swivel in relation to the central core and optionally permits the central core to slide in relation to the lower plate. This sliding of the central core in relation to the lower plate is an essential characteristic, as it must allow spontaneous positioning of the core in the ideal position to absorb constraints imposed on the prosthesis, during movements made by the patient wearing the prosthesis. The displacement of the core, co-operating with at least a plate about an uneven surface, enables an inclination between the plates of the prosthesis which facilitates the mobility of the patient wearing the prosthesis. The displacement of the core also prevents it from creeping when subjected to major constraints.

In this context, it is significant to propose a prosthesis which allows to impose a permanent inclination between the plates and induces, for example, lordosis. Depending on the disorder of the spinal column of the patient wearing the prosthesis, it is sometimes preferable that the prosthesis allows a correction of this disorder. In line with the wishes of the surgeon, the displacement of the core should be restricted in at least one direction. However, when the patient moves, the relative position of the elements of the prosthesis can be modified, within the permitted range of displacement.

One aim of some embodiments of the present invention is to propose an intervertebral disc prosthesis allowing limited movements of the different pieces of the prosthesis between one another and comprising a core used to restrict its displacement in at least one direction.

SUMMARY

An intervertebral disc prosthesis includes at least three pieces including a first plate, a second plate, and a mobile core, at least in rotation, at least in relation to one of the plates, the core having a curved surface in contact with at least a part of a complementary curved surface of the first plate, and a substantially flat surface in contact with at least a part of a substantially flat of the second, male and female co-operation means situated near the periphery of the second plate and of the core allowing, to limit or prevent, the movements in translation of the core in relation to the second plate to along an axis substantially parallel to the substantially flat surfaces, and allowing to limit or prevent the movements in rotation of the core in relation to the second plate, about an axis substantially perpendicular to the substantially flat surfaces, wherein the top of the curved surface of the core is off centre, in at least one direction, in relation to the geometric centre of this curved surface of the core.

According to another embodiment, the rest position of the core, that being when the patient is motionless, is shifted in the opposite direction to that of the off centre of the top of the curved surface of the core, thanks to the fact that the axes of symmetry of the first and second plates are aligned when the plates are anchored on the vertebrae and that the curved surface of the first plate, complementary with the curved surface of the core, induces the aligning of the off-centre top of this curved surface of the core with the axes of symmetry of the plates and therefore a shifting of the core in the opposite direction to that of the off centre of the top of its curved surface, which provokes a bringing together of the co-operation means present on the core and those present on the second plate, this bringing together consequently limits the displacement of the core in the opposite direction to that of the off centre of the top of its curved surface.

According to another embodiment, the same plates can be assembled with different cores, the difference between the cores consisting in the position of the top of their curved surface in relation to the centre of this curved surface of the core.

According to another embodiment, the same cores can be assembled with different plates, the difference between the plates consisting in the angle between the median planes representing the upper and lower surfaces of the plates.

According to another embodiment, an angle between the upper surface of the upper plate and the lower surface of the second plate can be imposed either by the fact that the median planes representing the upper and lower surfaces of the second plate and/or the first plate create an angle, or by restricting, thanks to the co-operation means, movements of the core about a position imposing an inclination of at least one of the plates.

According to another embodiment, the same plates can be assembled with cores of different thicknesses and/or sizes.

According to another embodiment, the curved surface of the core is a convex upper surface of the core and the curved surface of the first plate is a concave part of the lower surface of the upper plate.

According to another embodiment, the dimensions of each male co-operation means are slightly less than those of each female co-operation means so as to allow slight clearance between the core and the second plate.

According to another embodiment, the dimensions of each male means are substantially the same as those of each female means so as to prevent any clearance between the core and the second plate.

According to another embodiment, the core is made of polyethylene.

According to another embodiment, first and second plates are made of metal.

According to another embodiment, the second plate comprises female means co-operating with male means of the core.

According to another embodiment, the male means of the core are two contact plates situated on the two side edges of the core and the female means of the second plate are four walls situated, in pairs, on each of the two lateral edges of the second plate.

According to another embodiment, the walls forming the female co-operation means of the second plate are curved toward the centre of the prosthesis, so as to cover at least a part of the male means of the core and to prevent it from lifting.

According to another embodiment, the second plate comprises male means co-operating with female means of the core.

According to another embodiment, the male means of the second plate are two contact plates facing one another on two edges of the prosthesis, and the female means of the core are two recesses.

According to another embodiment, the male means of the second plate are two walls facing one another in the vicinity of two edges of the prosthesis, and the female means of the core are recesses.

According to another embodiment, the male means of the second plate are two nibs curved toward the interior of the prosthesis and facing one another on two edges of the prosthesis, and the female means of the core are two recesses.

According to another embodiment, at least one of the nibs is replaced by a contact plate fitted with a bore on which is fixed a lug by way of a pin penetrating the bore.

According to another embodiment, the first plate is bulged on at least a part of its upper surface to adapt to the form of the vertebrae.

BRIEF DESCRIPTION OF THE DRAWINGS

Other features and advantages of the various embodiments are in the description herein below, given in reference to the attached drawings, in which.

DETAILED DESCRIPTION OF PREFERRED EMBODIMENTS

The intervertebral disc prosthesis according to one embodiment of the present invention is constituted in a first plate (1) articulated in relation to a second plate (2) by means of a core (3), as evident in particular in FIGS. 2a to 2d. In the following description, the first plate (1) is called the upper plate and the second plate (2) is called the lower plate, according to the orientation given to the prosthesis shown in the drawings. The prosthesis herein described could also be inversely oriented between the vertebrae, so that the first plate (1) would be the lower plate and the second plate (2) would be the upper plate. As described below, the first plate comprises a curved surface (concave or convex) cooperating with a curved and complementary surface (convex or concave) of the nucleus and the second plate comprises a substantially flat surface cooperating with a substantially flat surface of the nucleus. These various surfaces described can belong to any of the first and second plate of the prosthesis without departing from the scope of the invention.

An advantage of the prosthesis according to this embodiment of the present invention is that it comprises simple pieces which can be dimensioned in order to be adapted to the different vertebrae of the spinal column.

The core (3) is of slight thickness (from 3 to 15 mm, depending on the vertebrae between which the prosthesis is to be inserted). For good absorption of the constraints, the core (3) could, for example, be made of polyethylene, a compressible material simulating the physical properties of elasticity of natural intervertebral discs.

The core (3) preferably has a convex part (30) on at least a part of at least one of its upper and lower surfaces. Preferably, the core (3) also has male or female co-operation means (33) complementary with respectively female or male co-operation means (23) present on at least one of the plates (1, 2).

Figure 1A:
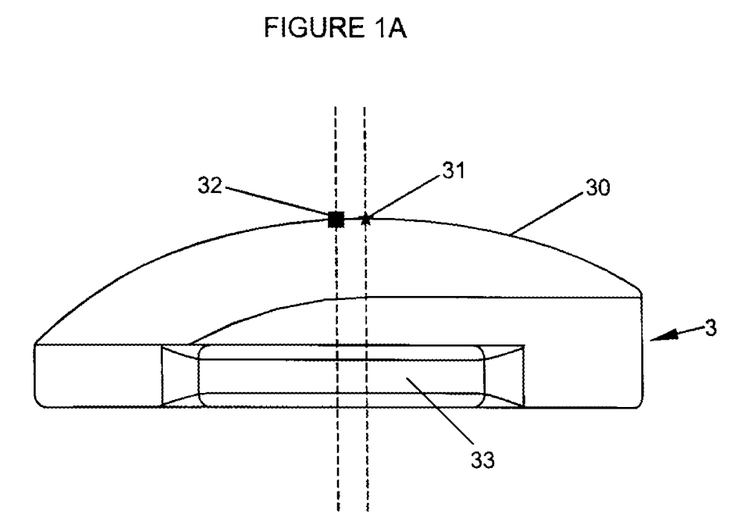
FIGS. 1a and 1b respectively illustrate, a side view and a top view of the core of the prosthesis according to one embodiment of the invention, FIGS. 2a and 2b respectively illustrate a front view and a side view of the prosthesis, in a first embodiment of the invention, and FIGS. 2c and 2d respectively illustrate a front view in perspective and a side view of the prosthesis, in a second embodiment of the invention, FIGS. 3a and 3b respectively illustrate a top view and a cross section view according to the plan A-A in FIG. 3a, of the lower plate of the prosthesis in an embodiment of the invention.
Figure 1B:
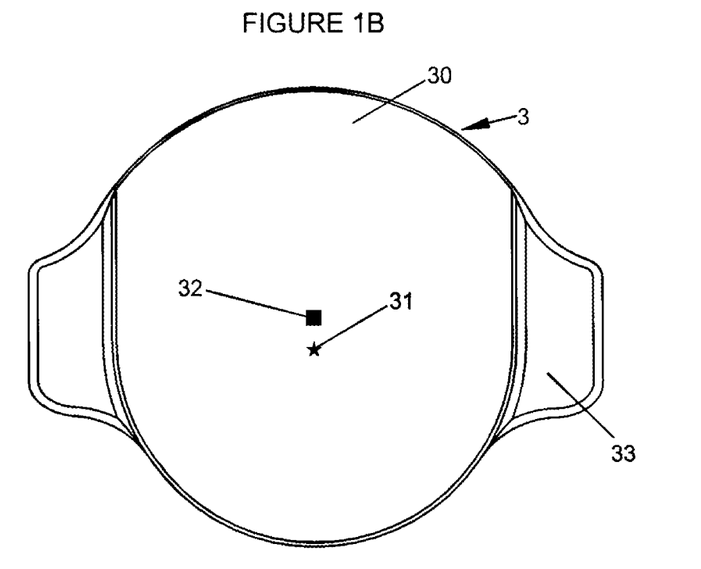

The description of one of these embodiments will now be dealt with in reference to FIGS. 1 to 3. In this embodiment, it is the upper surface of the core (3) which has a convex part (30), evident particularly in FIG. 1a. This convex surface (30) of the core (3) is complementary with a concave part (10) of the upper plate (1), evident particularly in FIGS. 3d and 3e. This concave part (10) allows to incline the upper plate (1) when the patient wearing the prosthesis bends over. The lower surface of the core (3) and the upper surface of the lower plate (2) could be plane so as to permit clearance of the core (3) in relation to the lower plate (2), both in translation according to an axis substantially parallel to the lower plate (2), and in rotation about an axis substantially perpendicular to the lower plate (2). During movements by the patient wearing the prosthesis, this inclination of the upper plate (1) and this clearance of the core will allow displacement of the core (3) towards the ideal position to absorb the constraints applied to the prosthesis. The movement between the upper plate (1) and the core (3), as well as the clearance of the core (3) in relation to the lower plate (2) thus allow the patient to move, and, optionally, to eliminate the defects of positioning the prosthesis. This clearance likewise has the advantage of preventing premature wear due to the constraints applied to the prosthesis.

Figure 2A:
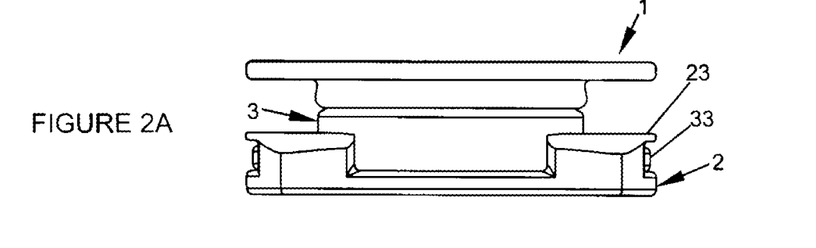
Figure 2B:
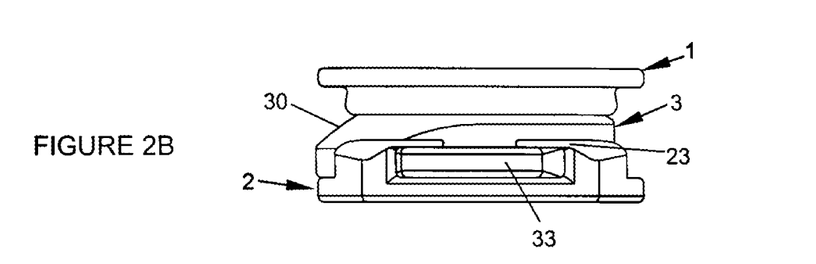
Figure 2C:
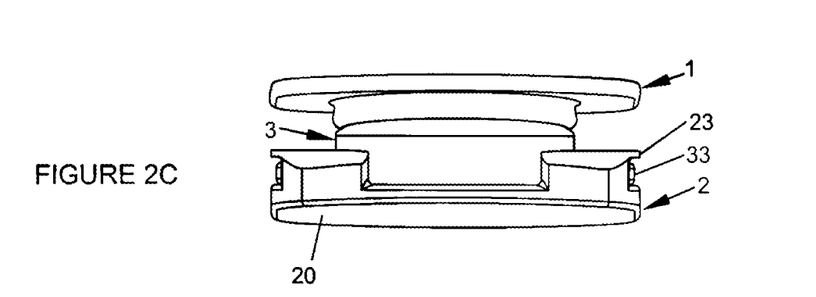
Figure 2D:
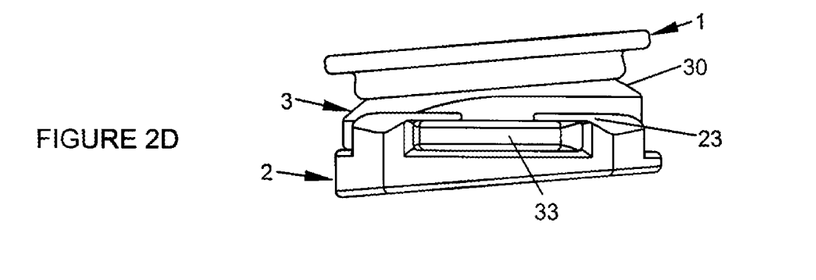

The intervertebral disc prosthesis according to some embodiments allows, for example, to correct the defects of lordosis. The presence of an angle between the upper plate (1) and the lower plate (2) of the prosthesis could be desirable. Such an angle could be obtained by making an upper plate, whose median planes representing its lower and upper surfaces create an angle. Another possibility involves the lower plate whereof the median planes representing its lower and upper surfaces create an angle, as illustrated in FIGS. 2c and 2d, in which the lower surface (20) of the lower plate (2) create an angle with its upper surface. Another possibility to obtain such an angle is only allowed by prostheses of the same type as those of preferred embodiments of the invention and consists in a slightly offset position of the core in relation to the centre of the prosthesis. This slightly offset position of the core can, for example, be maintained thanks to an adjustable positioning of the male and female co-operation means between themselves. If the surgeon wishes, for example, that the prosthesis induces lordosis which remains within a range of values, he will select a prosthesis whose core (3) can have slight clearance in translation and in rotation in relation to the lower plate (2), but about a position imposing a slight permanent inclination of at least one of the plates, thanks to an accurate adjustment of the co-operation means between the core and the lower plate (2).

Figure 3A:
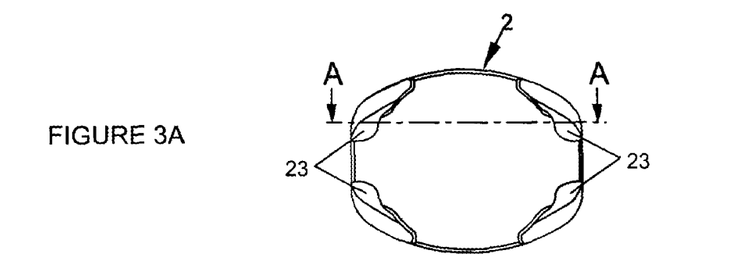
Figure 3B:
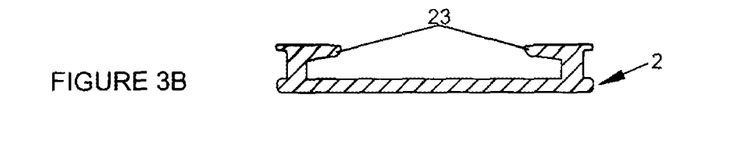
Figure 3C:
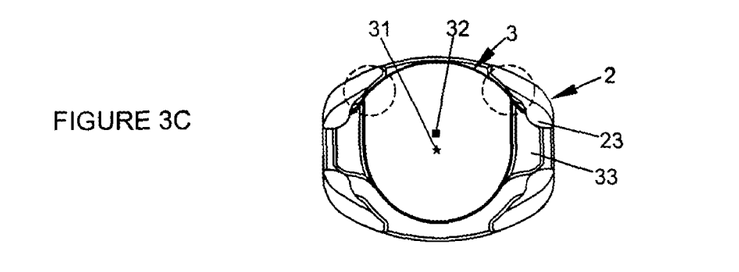
FIG. 3c illustrates a top view of the lower plate with the core and FIGS. 3d and 3e respectively illustrate a top view and a cross section view according to the plan B-B in FIG. 3d, of the upper plate of the prosthesis in an embodiment of the invention.
Figure 3D:
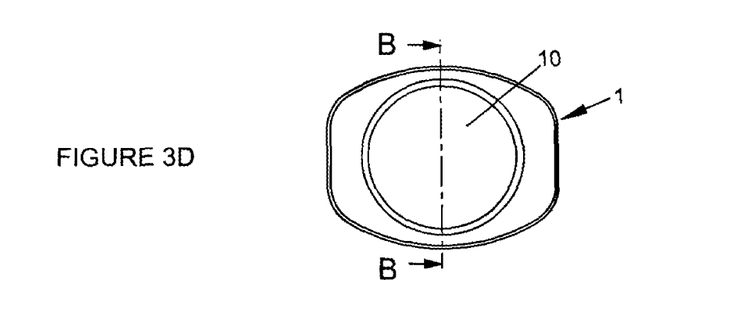
Figure 3E:
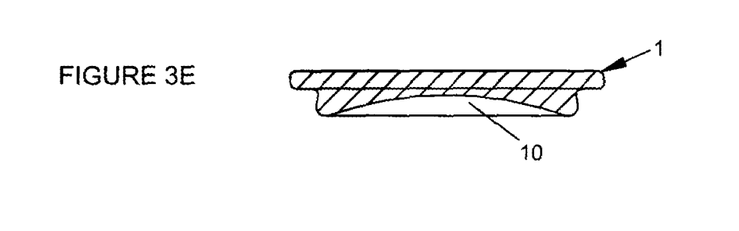

The prosthesis according to preferred embodiments has a characteristic which improves its behaviour once positioned between the vertebrae of the patient. This feature resides in the fact that the top (31) of the curved surface (30) of the core (3), i.e. the highest point (31) of this curved surface (in a side view), is off centre in relation to the geometric centre (32) of this curved surface (30) of the core (3), i.e. the point (32) equidistant from any point in the periphery of the curved surface (in a top view) or the intersection of the longitudinal and the transversal axes of symmetry of the core (3). In the examples shown, the curved surface (30) of the core (3) is convex and the curved surface of the first plate is a concave part (10) of the lower surface of the upper plate (1), but the various elements of the instant prosthesis can be rearranged so that the convex surface is on one of the plates and the concave surface is on the core. The centre of the concave part (10) of the upper plate (1), complementary with this convex surface (30), swivels around this top (31) of the convex surface (30). Although being mobile about this top (31), the upper plate (1) will therefore be on average centred on the top (31) of the convex surface (30) of the core (3). The vertical axes which pass through the centres of two adjacent vertebrae are generally aligned, even though they can be slightly inclined depending on the movements of the patient or depending on the zone in question of the spinal column. It is therefore important that the vertical axes which pass through the centres of the plates (1, 2) and through the top (31) of the convex surface (30) of the core are also aligned. So that these axes are aligned, the off-centre top (31) of the convex surface (30) of the core (3) must be in the axis of the centres of the plates and therefore of the core (3) that being off centre in relation to the lower plate (2). Thus the rest position of the core (3) will be off centre in relation to the centre of the prosthesis. As illustrated in FIG. 3C, in which the upper plate (1) is not shown for reasons of clarity, the core is off centre in relation to the centre of the prosthesis and the co-operation means (33) of the core (3) are in contact with the co-operation means (23) of the lower plate (2), in the zones encircled with a dotted line. FIG. 2B also emphasises this shift of the core (3) in relation to the side view of the centre of the prosthesis. The shifting of the core (3) and the contact between the co-operation means (33) and those of the lower plate (23) will also restrict the displacement of the core (3) in the opposite direction to that of the off centre of the top (31) of the convex surface (30). We can then choose the direction and amplitude of the shift to be made to the top (31) of the convex surface (30) of the core (3), in order to obtain a desired reduction in displacement. The core (3) can then, for example, only be displaced in the direction of the shifting of the top (31) in relation to the centre (32) of the convex surface (30) of the core (3). If the patient wearing the prosthesis according to this embodiment bends over in the opposite direction to this shifting of the top (31), the core (3) can then move in the direction of this shifting of the top (31), thus reducing the shifting between the vertical axes passing through the centres of the plates, which is what would happen if the top (31) of the convex surface (30) of the core (3) was not off centre. An essential consequence of this feature is therefore that it allows to permanently restrict the shifting between the vertical axes passing through the centres of the vertebrae, even when the patient bends over. For example, we can choose a core (3) whose top (31) of its convex surface (30) is off centre to the rear so that the core, in the rest position, is completely off centre to the front of the prosthesis and can not be displaced further forward. Such a core therefore restricts the displacement of the core to the front and reduces the angle to which the patient can bend backwards. However, if the patient bends forward, the upper plate (1) inclines to the front, thus inducing a shifting of the vertical axis passing through its centre, in relation to the vertical axis passing through the centre of the lower plate (2). However, this shifting is eliminated by displacing the core (3) to the rear of the prosthesis. This shifting is better eliminated when the upper plate is mobile about the off-centre top (31) of the convex surface (30) of the core (3). The core (3) with an off-centre top (31) then wedges into the rear of its opening in the prosthesis and allows a better alignment of the vertical axes passing through the centres of the plates than a core with an off-centre top does.

Another advantage of some embodiments relates to the implanting of prostheses between the vertebrae of a recipient patient. During implantation of prostheses with mobile cores, the core of the prosthesis has a tendency to move to a far end of its stroke in its opening within the prosthesis. The patient is thus equipped with a prosthesis which imposes a slight inclination to his/her spinal column. This inclination can be eliminated thanks to the movements of the patient as soon as he/she has recovered from the operation. However, this inclination provokes considerable discomfort for the patient. Thanks to the off-centre position of the top (31) of the core (3) of the prosthesis according to preferred embodiments, the core (3) would tend to move into an off-centre rest position, in which the top (31) is aligned in relation to the axes of the upper and lower plates. Thanks to this spontaneous alignment of the axes of the prosthesis, no inclination of the plates will be imposed in the rest position and the patient will have been equipped with a prosthesis that does not provoke any discomfort.

In the embodiment in FIGS. 1 to 3, the core (3) has male co-operation means (33) complementary with female co-operation means (23) present on the lower plate (2). The male co-operation means (33) of the core (3) are, for example, hasps substantially parallelepiped in shape, as particularly visible in FIGS. 1*a* and 1*b*. The female co-operation means (23) can, as particularly visible in FIGS. 3*a* and 3*b*, consist, for example, in four walls situated, in pairs, on each of the two side edges of the lower plate (2). These walls could be curved toward the centre of the prosthesis, so as to cover at least a part of the male co-operation means (33) of the core (3) and avoid lifting the core (3) and the upper plate (1). In this embodiment illustrated in FIGS. 1 to 3, the dimensions of each male means (33) of the core (3) are slightly less than those of each female means (22) of the lower plate (2), so as to allow a restricted clearance of the core (3) in relation to the lower plate (2), both in translation according to an axis substantially parallel to the lower plate (2), and in rotation about an axis substantially perpendicular to the lower plate (2). These co-operation means (23, 33) also prevent the core (3) from ejecting out of the prosthesis, in the event of too much constraint on the prosthesis.

In an alternative embodiment not shown, the dimensions of each male co-operation means (33) of the core (3) are substantially the same as those of each female co-operation means (23) of the lower plate (2), so as to avoid any clearance of the core (3) in relation to the lower plate (2), both in translation and in rotation. In the latter case, the only permitted movement of the prosthesis is that of the upper plate (1) in relation to the core (3).

In an alternative embodiment not shown, the core (3) has female co-operation means, consisting, for example, in complementary recesses of the male means present on the lower plate (2). These male means of the lower plate (2) can consist, for example, in two contact plates or two nibs, for example curved toward the interior of the prosthesis and facing one another on two edges of the lower plate (2).

In another alternative embodiment not shown, the lower plate (2) has dowels. The core (3), by way of complement, has two wells under its lower surface. The dimensions of the dowels of the lower plate (2) and of the wells of the core (3)

will be adapted according to the desired result, by choice, of slight clearance of the core in translation and in rotation or any clearance.

In an alternative embodiment not shown, a part of the upper surface of the upper plate (1) is bulged, so as to better adapt to the vertebra on which the prosthesis is intended to be placed, the lower surface of the vertebrae being hollow. The bulged part of the upper plate (1) is then situated in the front part of the upper plate. The lower plate (2) is substantially plane as its lower surface has no need to be bulged or hollow, since the upper surface of the vertebrae is substantially flat.

It must be evident for specialists that the invention allows embodiments in numerous other specific forms without departing from the scope of application of the invention as claimed. As a consequence, the embodiments must be considered by way of illustration, but can be modified within the scope defined by the range of the attached claims, and the invention does not have to be limited to the details given above.

The invention claimed is:

1. An intervertebral prosthesis for insertion between a first vertebra and a second vertebra comprising:
    a first plate having a geometric center and a first curved bearing surface disposed on an opposite side of the first plate;
    a second plate having a geometric center and a second flat bearing surface disposed on an opposite side of the second plate; and
    a mobile core having a flat side and an opposing curved side and a height between the flat side and the curved side, the flat side configured for complementary engagement with the second flat bearing surface and the curved side configured for complementary engagement with the first curved bearing surface, the curved side of the core having a top point defined by the height of the core and a center point defined by the geometric center of the curved side of the core, with the center point offset from the top point;
    the core having a rest position in which geometric center of the first plate, the geometric center of the second plate, and the top point of the core are aligned along a common axis.

2. The intervertebral prosthesis of claim 1 further comprising a core stop located at a lateral edge of the core.

3. The intervertebral prosthesis of claim 2 in which the core stop comprises a projection configured to engage a pair of incurvate walls disposed along a side of the first plate or the second plate.

4. The intervertebral prosthesis of claim 2 in which the core stop comprises a recess configured to engage a projection disposed along a side of the first plate or the second plate.

5. The intervertebral prosthesis of claim 4 in which the projection comprises a wall configured to enter the recess.

6. The intervertebral prosthesis of claim 4 in which the projection comprises a incurvate nib.

7. The intervertebral prosthesis of claim 1 in which a peripheral wall joins the flat side of the core and the curved side of the core, and the peripheral wall has a first height that is constant along a first portion of the core periphery defined by the peripheral wall.

8. The intervertebral prosthesis of claim 7 in which the peripheral wall has a second height that is constant along a second portion of the core periphery defined by the peripheral wall.

9. An intervertebral prosthesis for insertion between a first vertebra and a second vertebra, the prosthesis having a center and comprising:
    a first plate having a first curved bearing surface disposed on a side of the first plate;
    a second plate having, the prosthesis having a center and a second flat bearing surface disposed on a side of the second plate; and
    a mobile core having a flat side and an opposing curved side and a height between the flat side and the curved side, the flat side configured for complementary engagement with the second flat bearing surface and the curved side configured for complementary engagement with the first curved bearing surface, the curved side of the core having a top point defined by the height of the core and a center point defined by the geometric center of the curved side of the core, with the center point offset from the top point and the top point laying away from the edge of the curved side;
    the core having a rest position in which the core is off-center in relation to the center of the prosthesis.

10. The intervertebral prosthesis of claim 9 further comprising a core stop located at a lateral edge of the core.

11. The intervertebral prosthesis of claim 10 in which the core stop comprises a projection configured to engage a pair of incurvate walls disposed along a side of the first plate or the second plate.

12. The intervertebral prosthesis of claim 10 in which the core stop comprises a recess configured to engage a projection disposed along a side of the first plate or the second plate.

13. The intervertebral prosthesis of claim 12 in which the projection comprises a wall configured to enter the recess.

14. The intervertebral prosthesis of claim 9 in which a peripheral wall joins the flat side of the core and the curved side of the core, and the peripheral wall has a first height that is constant along a first portion of the core periphery defined by the peripheral wall.

15. The intervertebral prosthesis of claim 14 in which the peripheral wall has a second height that is constant along a second portion of the core periphery defined by the peripheral wall.

16. An intervertebral prosthesis for insertion between a first vertebra and a second vertebra comprising:
    a first plate having a first curved bearing surface disposed on a side of the first plate, the first curved bearing surface having a length;
    a second plate having, the prosthesis having a center and a second flat bearing surface disposed on a side of the second plate; and
    a mobile core having a flat side and an opposing curved side and a height between the flat side and the curved side, the flat side configured for complementary engagement with the second flat bearing surface and the curved side configured for complementary engagement with the first curved bearing surface, the curved side of the core having a top point defined by the height of the core and a center point defined by the geometric center of the curved side of the core, with the center point offset from the top point and the top point laying away from the edge of the curved side, the curved side of the core having a length along an arc on the curved side passing through the top point and the center point that is greater than a length along an arc on the first curved bearing surface.

17. The intervertebral prosthesis of claim 16 further comprising a projection located at a lateral edge of the core and configured to engage a pair of incurvate walls disposed along a side of the first plate or the second plate.

18. The intervertebral prosthesis of claim 16 further comprising recess located at a lateral edge of the core and a wall disposed along a side of the second plate configured to enter the recess and limit translational and rotational movements of the core along the second flat bearing surface.

19. The intervertebral prosthesis of claim 16 in which a peripheral wall joins the flat side of the core and the curved side of the core, and the peripheral wall has a first height that is constant along a first portion of the core periphery defined by the peripheral wall.

20. The intervertebral prosthesis of claim 19 in which the peripheral wall has a second height that is constant along a second portion of the core periphery defined by the peripheral wall.

* * * * *